US007179656B2

(12) United States Patent
Lecloux et al.

(10) Patent No.: US 7,179,656 B2
(45) Date of Patent: Feb. 20, 2007

(54) SUBLIMATION SCREENING TEST AND APPARATUS

(75) Inventors: Daniel David Lecloux, Wilmington, DE (US); Steven J. Medwin, Binghamton, NY (US); Eric Maurice Smith, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 787 days.

(21) Appl. No.: 10/188,517

(22) Filed: Jul. 3, 2002

(65) Prior Publication Data

US 2003/0054565 A1    Mar. 20, 2003

Related U.S. Application Data

(60) Provisional application No. 60/305,955, filed on Jul. 17, 2001.

(51) Int. Cl.
*G01N 1/22* (2006.01)
(52) U.S. Cl. .................. 436/181; 436/180; 422/100
(58) Field of Classification Search ............ 436/180, 436/181; 422/100
See application file for complete search history.

(56) References Cited

U.S. PATENT DOCUMENTS 3,396,152 A    8/1968    Henning et al.
3,546,920 A    12/1970   Webb et al.
3,847,200 A    11/1974   Kopp et al.
4,501,719 A *  2/1985    Williams ............... 422/102
5,589,550 A    12/1996   Manley et al.
6,464,943 B1 * 10/2002   Yiu ....................... 422/100
6,566,144 B1 * 5/2003    Madril et al. ........... 436/177

FOREIGN PATENT DOCUMENTS

| CH | 472231 | 5/1969 |
|----|--------|--------|
| DE | 937260 | 12/1955 |
| EP | 181 408 | 5/1986 |
| EP | 458 164 | 11/1991 |
| EP | 679 663 | 11/1995 |
| GB | 1044773 | 10/1966 |
| GB | 1156115 | 2/1988 |
| WO | WO 9010654 | 9/1990 |
| WO | WO 9709353 | 3/1997 |

* cited by examiner

*Primary Examiner*—Jill Warden
*Assistant Examiner*—Natalia Levkovich

(57) ABSTRACT

Disclosed is an apparatus for rapidly screening chemicals for their ability to sublime. The apparatus consists of a heated well plate, where the chemicals are deposited, and a cooled finger plate, holding fingers that penetrate each well. The two plates touch at only the perimeter in order to facilitate a vacuum seal and to reduce any thermal transfer.

26 Claims, 4 Drawing Sheets

SUBLIMATION SCREENING TEST AND APPARATUS

FIELD OF INVENTION

The invention concerns an apparatus and method to rapidly screen chemicals for their ability to sublime. The apparatus consists of a heated well plate, where the chemicals are deposited and a cooled finger plate with fingers that penetrate each well. The two plates touch only at the perimeter in order to facilitate a vacuum seal and to reduce thermal transfer.

TECHNICAL BACKGROUND

Many technologies require the use of thin, uniform coatings, which are typically prepared using chemical vapor deposition and other techniques in which sublimation is a key step. When performing research in these areas, there is a need to rapidly screen thousands of chemicals for their ability to sublime. Currently, it takes several hours using commercially available apparatus to determine if a single compound will sublime. When taking a combinatorial approach to finding suitable compounds, the testing time is slow and labor-intensive. There is a need for a method to rapidly and easily screen large numbers of compounds for the ability to sublime at particular conditions. In particular, there is a need for a method that can detect the presence of the sublimed materials clearly and rapidly, and that can be easily assembled and cleaned.

SUMMARY OF THE INVENTION

Described herein is an apparatus, comprising: a) a well-plate containing one well or a plurality of wells; b) a finger plate located above the well plate forming a plate free space, wherein the finger plate contains one or more recesses; c) one or more fingers located inside each recess, wherein each of the fingers extend downwards into one of the wells, forming a well space between each finger and the corresponding well and recess; wherein the well space and the plate free space together form a channel; d) a means for sealing the channel around the outside perimeter of the wells and fingers; e) a means for heating the well plate; and f) a means for cooling the fingers such that the fingers are at a lower temperature than the wells.

Also disclosed is an apparatus, comprising: a) a well-plate containing one well or a plurality of wells; b) a finger plate located above the well plate forming a plate free space, wherein the finger plate contains one or more recesses; c) one or more fingers located inside each recess, wherein each of the fingers extend downwards into one of the wells, forming a well space between each finger and the corresponding well and recess; wherein the well space and the plate free space together form a channel; d) a means for drawing a vacuum connected to the channel; e) a means for sealing the channel around the outside perimeter of the wells and fingers such that the plate free space and continuous channel can maintain a vacuum; f) a means for heating the well plate; and g) a means for cooling the fingers such that the fingers are at a lower temperature than the wells.

Also disclosed is a method for testing the sublimation potential of a compound, comprising: I) placing one or more compounds in the bottom of one or more wells, wherein only one compound is placed in each well, and wherein said wells are located in an apparatus, comprising: a) a well-plate containing one well or a plurality of wells; b) a finger plate located above the well plate forming a plate free space, wherein the finger plate contains one or more recesses; c) one or more fingers located inside each recess, wherein each of the fingers extend downwards into one of the wells, forming a well space between each finger and the corresponding well and recess; wherein the well space and the plate free space together form a channel; d) a means for sealing the channel around the outside perimeter of the wells and fingers; e) a means for heating the well plate; and f) a means for cooling the fingers such that the fingers are at a lower temperature than the wells; II) cooling the fingers to a temperature of −20° C. to 100° C.; III) heating the wells to a temperature of 100° C. to 300° C.; IV) removing the finger plate; and V) detecting the presence of the each compound on the bottom of each finger.

Also disclosed is a method for testing the sublimation potential of a compound, comprising: I) placing one or more compounds in the bottom of one or more wells, wherein only one compound is placed in each well, and wherein said wells are located in an apparatus, comprising: a) a well-plate containing one well or a plurality of wells; b) a finger plate located above the well plate forming a plate free space, wherein the finger plate contains one or more recesses; c) one or more fingers located inside each recess, wherein each of the fingers extend downwards into one of the wells, forming a well space between each finger and the corresponding well and recess; wherein the well space and the plate free space together form a channel; d) a means for drawing a vacuum connected to the channel; e) a means for sealing the channel around the outside perimeter of the wells and fingers such that the plate free space and continuous channel can maintain a vacuum; f) a means for heating the well plate; and g) a means for cooling the fingers such that the fingers are at a lower temperature than the wells; II) creating a vacuum within the channel; III) cooling the fingers to a temperature of −20° C. to 100° C.; IV) heating the wells to a temperature of 100° C. to 300° C.; V) removing the finger plate; and VI) detecting the presence of the each compound on the bottom of each finger.

DETAILED DESCRIPTION OF THE INVENTION

Figure 1:
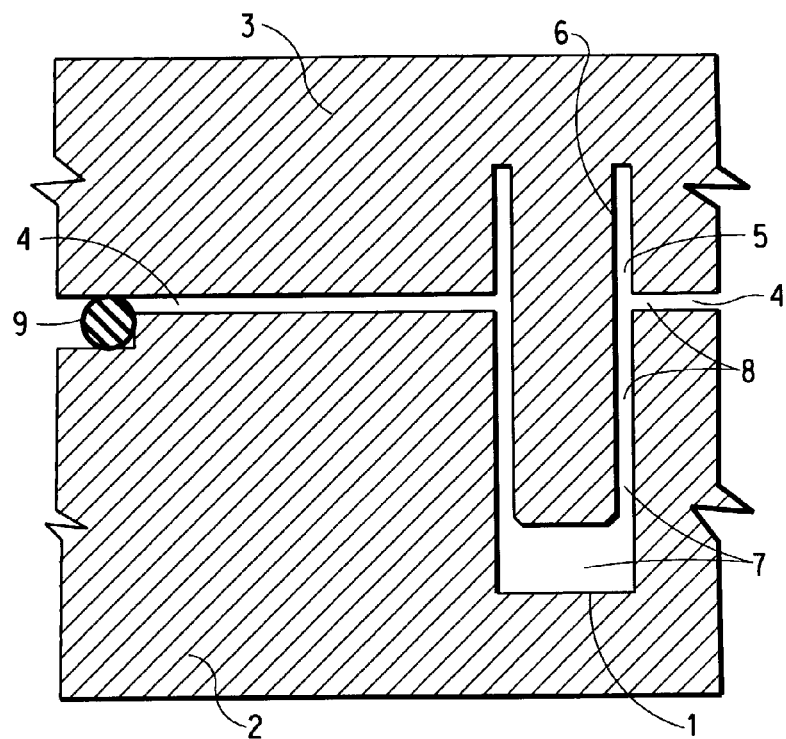
FIG. 1 is a cross-sectional side view of the relationship between the well, finger, and channel.

The present invention is an apparatus to test the sublimation potential of one or more compounds simultaneously. The apparatus consists of one or more wells, located in a well plate, in which the compound to be tested is placed. Over the well plate is a finger plate containing one or more recesses, where each recess contains a finger which extends downwards into the corresponding well. The fingers may optionally extend upwards through the finger plate to facilitate cooling. Each well has a corresponding finger, and each finger extends down into the corresponding well. Each finger does not touch its corresponding well at any point. The total space formed between the finger and its corresponding well and recess along the sides and the bottom is called the well channel. The wells and fingers can be of any size and shape, such as square, round, or hexagonal, providing that each finger can be removed from its corresponding well. A cylindrical shape for both is preferred for ease of use. The finger is preferably 0.70 in (17.8 mm) long (from bottom of recess to tip of pin) by 0.188 in (4.78 mm) diameter, and the well is preferably 0.50 in (12.7 mm) deep by 0.25 in (6.4 mm) diameter. A flat bottom for the well and fingers is also preferred. The distance between the bottom of the well and the bottom of the pin is greater than zero, and no greater than the calculated mean free path. The mean free path can be calculated using the equation $$\lambda = \frac{RT}{\sqrt{2}\,\pi d^2 N_a P}$$

where R is the gas constant, T is temperature, d is the diameter of the molecule, $N_a$ is Avogadro's number, and P is the pressure. The free mean path is used so that an individual molecule, when subliming, will theoretically impact the bottom of the pin before it impacts another molecule. A preferred distance is ⅛ inch (3.18 mm).

The finger plate is located above the well plate at a distance of about 0.015 in (0.38 mm), forming a plate free space. The plate free space and the well channel together form a continuous space called the channel, which is further connected to a means for drawing a vacuum, preferably a vacuum pump. By "vacuum" it is meant a pressure equal to or less than current atmospheric pressure. The operating pressure is dependent upon the distance between the well plate and the bottom of the finger. For each distance, the mean path equation from above will give the corresponding maximum pressure that can be used. Preferably, the pressure is at least $10^{-2}$ torr (1.3 Pa).

There is a means for sealing the channel around the outside perimeter of the well or wells such that the desired vacuum can be maintained in the channel. The evacuated space functions as a heat insulator and aids in increasing sublimation or decreasing sublimation temperature.

The means for sealing can include, but is not limited to, an o-ring or a gasket. An o-ring is a preferred embodiment, preferably made of a material that can function as a sealing means at the temperatures used. One such material is Kalrez® perfluoroelastomer (DuPont Dow Elastomers L.L.C.).

FIG. 1 depicts a portion of one embodiment of the instant invention. A well 1 is formed in a well plate 2. On top of the well plate 2 is a finger plate 3, forming a plate free space 4. The finger plate 3 contains a recess 5. Extending down from the recess 5 into the well 1 is a finger 6, forming a well space 7. The well space 7 and the plate free space 4 together form the channel 8. The channel is sealed by a means for sealing 9, in this embodiment an o-ring.

Another embodiment of the channel includes a network of interconnected channels in the finger plate located between the recesses, with one or more openings from each recess to a channel. The network of channels is connected to the means for drawing a vacuum either directly or through a manifold, to which all of the channels are connected. The network of channels and the manifold, when present, are considered part of the channel. The network of channels and the manifold are preferably round for ease of construction. The function of the network of channels is to supply vacuum and to prevent cross-contamination of the wells by the sublimed material. The cross sectional area of the channels is greater than the adjacent cross sectional area of the plate free space so that the path of least resistance to the vacuum is along the channels and so that any sublimed material from a well will condense and collect in the channel and not travel to and condense in a neighboring well. The channel diameter is preferably about 0.135 in (3.43 mm). The openings between the channels and the recesses are preferably located near the top of the recess, also to minimize cross-contamination.

Figure 2:
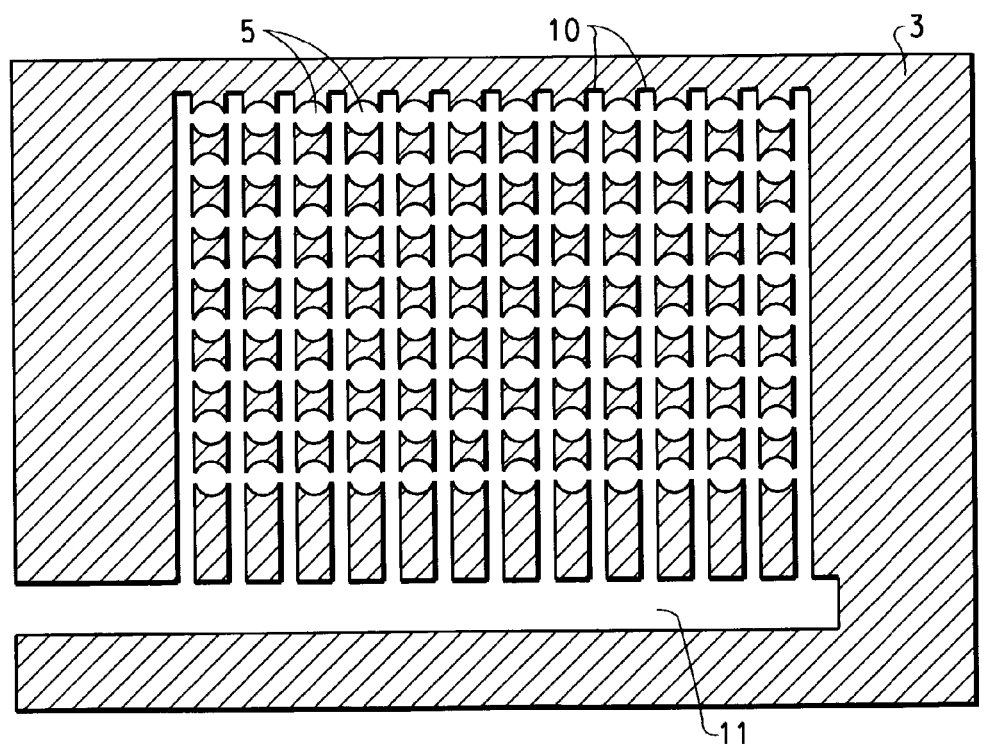
FIG. 2 is a top cross-sectional view through the finger plate of the additional channels and manifold connected to the recesses.

One embodiment is shown in FIG. 2. The finger plate 3 is shown, containing 96 recesses 5. Between and connected to at least one of each recess 5 are 13 channels 10, which all connect to the manifold 11. The manifold 11 contains an outlet 12, which is connected to the means for drawing a vacuum at the edge of the finger plate 3.

Figure 3A:
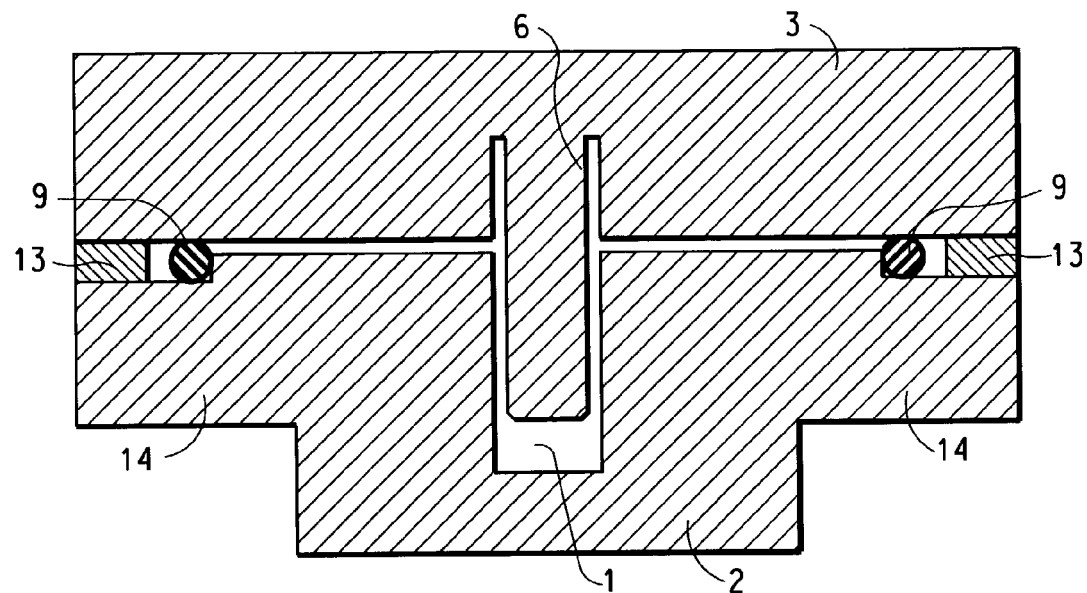
FIG. 3a is a side cross-sectional view of the well plate, illustrating the position of the lip to the sealing means.
Figure 3B:
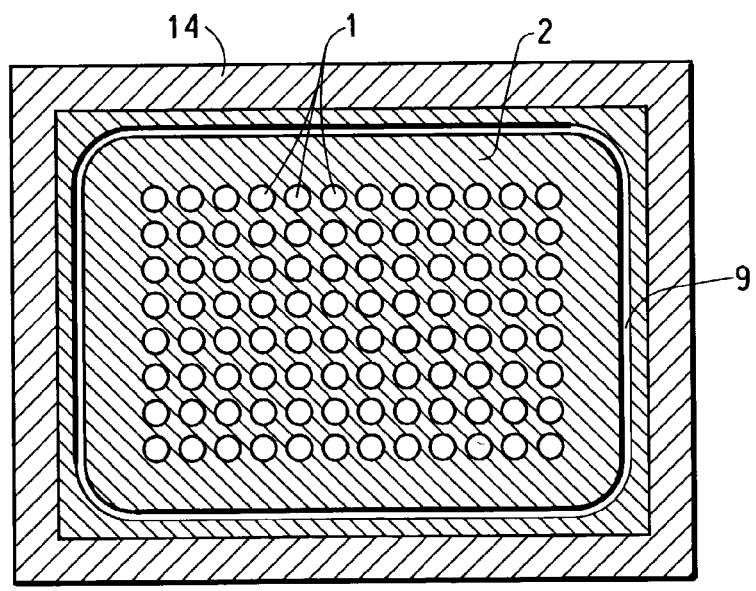
FIG. 3b is a top cross-sectional view of the well plate, illustrating the position of the lip to the sealing means.

Another embodiment includes a spacer located between the finger plate and the well plate. The function of the spacer is to maintain the plate free space at a particular dimension. When a less rigid sealing means such as an o-ring is used, the spacer also may function as a means to prevent the sealing means from being overly compressed, which could reduce the ability to vacuum seal the channel or could damage the sealing means. If the spacer is constructed of a structural insulating material such as ceramic, then it may also function to reduce heat transfer between the well plate and the finger plate. There may be more than one spacer located around the perimeter of the finger plate, or one continuous spacer Another embodiment includes a lip located around the perimeter of the well plate, on which the means for sealing is located. The lip will function to lower the temperature of the well plate around the means for sealing when the lip is not directly in contact with the heat source and if the spacer is a thermal conductor, by allowing the cold finger plate to cool the lip of the well plate. This allows materials to be used for the sealing means that would normally not be suitable for use at the desired temperature. Referring to FIG. 3a, there is shown a side cross-sectional view of the well plate 2 and the finger plate 3, illustrating the position of the lip 14 to the spacer 13 and the sealing means 9, in this embodiment an o-ring, and a well 1 with a finger 6. Referring to FIG. 3b, there is shown a top cross-sectional view of the well plate 2, illustrating the position of the lip 14 to the sealing means 9, in this embodiment an o-ring, and a plurality of wells 1.

The invention includes a means for heating the well plate and a means for cooling the finger plate. The heating means can be any means that uniformly heats the well plate to the desired temperature, such as but not limited to electric cartridge heaters, microwave heating, hot fluid, and infrared heating. A preferred means is a hot plate.

The means for cooling can be any means that uniformly cools the fingers to the desired temperature, such as but not limited to a chilled fluid. A preferred means is an enclosure located around the perimeter of the finger plate that contains either a circulating or static cold material, such as liquid nitrogen, chilled water or dry ice. A more preferred means is when the fingers extend upwards through the finger plate into the enclosure, such that the fingers are surrounded by the cold material, enabling rapid cooling of the fingers.

The heating means and the cooling means may be monitored and/or controlled. One method to monitor both means is through the use of thermocouples. Convenient sites for holes in which to insert the thermocouple are in the well plate underneath the well, and in holes drilled through one or more of the fingers.

Figure 4:
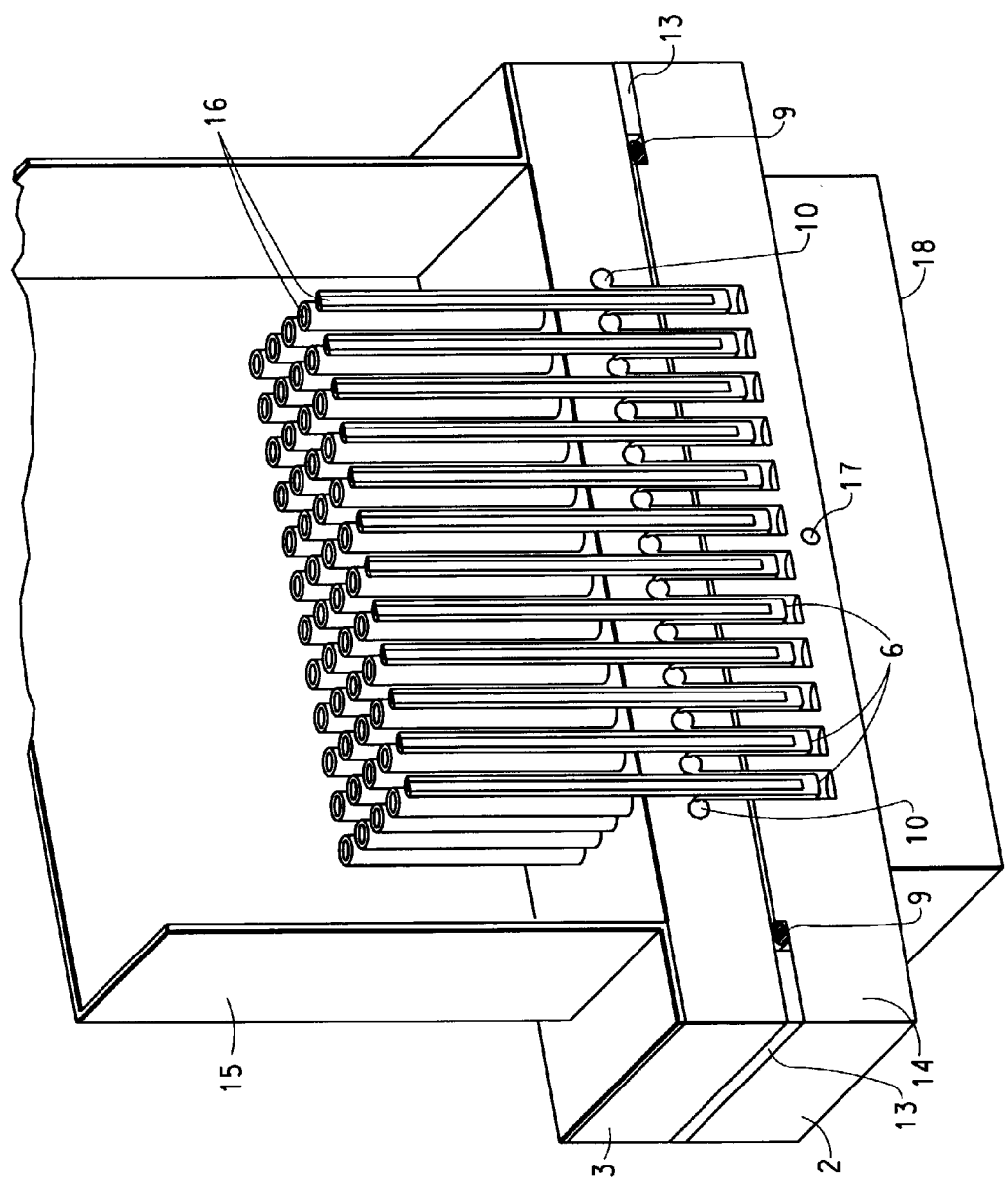
FIG. 4 is a cross-sectional side view of the assembled apparatus.

Referring to FIG. 4, there is shown a cross-sectional side view of an embodiment of the invention. The finger plate 3 is on top of the well plate 2, separated by a spacer 13. A plurality of fingers 6 are shown which extend upwards through the finger plate 3, and which are surrounded by an enclosure 15, suitable for retaining a cold material, functioning as a cooling means. The sealing means 9 shown in this embodiment is an o-ring. Holes 16 are located in each of the fingers to allow a thermocouple to be inserted at any finger. A hole 17 is shown under the wells 1 to allow a thermocouple to be inserted. Underneath the well plate 2 is a hot plate 18, suitable for use as a means for heating.

The well plate, finger plate, and fingers may be constructed out of any material that can be used at the desired temperatures without degradation or distortion. It is preferred that a material with a sufficiently high thermoconductivity be used, in order to allow sufficient heat transfer to occur. Stainless steel is a preferred material, with a smooth machined finish of 12□ inches/inches to minimize radiant heat transfer and facilitate cleaning.

The present invention also includes a method to test the sublimation potential of a compound, using the apparatus described above. One or more compounds are placed in the bottom of one or more wells described, with only one compound placed in each well. The fingers are cooled using a means for cooling as described above to a temperature of about −20° C. to about 100° C., preferably about −20° C. to about 0° C. If necessary to reach the desired pressure, the channel is evacuated either before or after cooling using a means for drawing vacuum as described above, preferably to at least $10^{-2}$ torr (1.33 Pa). The wells are next heated using the means for heating as described above to a temperature of about 100° C. to about 300° C.; preferably about 240° C. to about 260° C. The time that the wells are held at the maximum temperature is not critical, as the sublimation is very rapid and most likely completed before maximum temperature is reached. A preferred time is 5 minutes. Next, the wells and pins are brought to room temperature and the plate free space is brought to atmospheric pressure, if necessary. Finally, the finger plate is removed and the presence of the each compound is detected on the bottom of each finger.

The compounds are initially deposited onto the bottom of the wells such that the compound does not touch the bottom of the corresponding finger. Any method of deposition can be used that forms a relatively uniform, thin layer of compound, including but not limited to dusting of a powdered compound and pipetting of a liquid compound. A preferred method is pipetting of the compound dissolved in a solvent into the well and allowing the solvent to dry. A flat well bottom is preferred for this method.

The apparatus described above is convenient for robotic methods of deposition, allowing large numbers of compounds to be deposited into each well quickly and easily.

The temperatures and temperature differential used are chosen to maximize sublimation and are dependent on the compounds tested. The amount of vacuum is also dependent on the compounds tested, as lower pressures will increase sublimation and allow a smaller temperature differential to be used.

Any method of detecting the sublimed compound on the fingers can be used, including but not limited to visual, photographic and fluorescence detection, under visible, ultraviolet or infrared light. These methods are convenient for combinatorial screening as the sublimed compounds can be quickly and easily detected even when large numbers of compounds are being tested.

After sublimation, the apparatus, as described above, is easily dissembled to allow detection of sublimation. Use of a metal, such as stainless steel, for the well plate allows one to remove difficult residues after testing via thermal destruction in an oven.

EXAMPLE

The yellow luminescent material used in this Example, fac-lr(2-phenylpyridine)$_3$, was prepared as described in King, K. A.; Spellane, P. J.; Watts, R. J.; J Am. Chem. Soc. 1985, 107, 1431.

Figure 5:
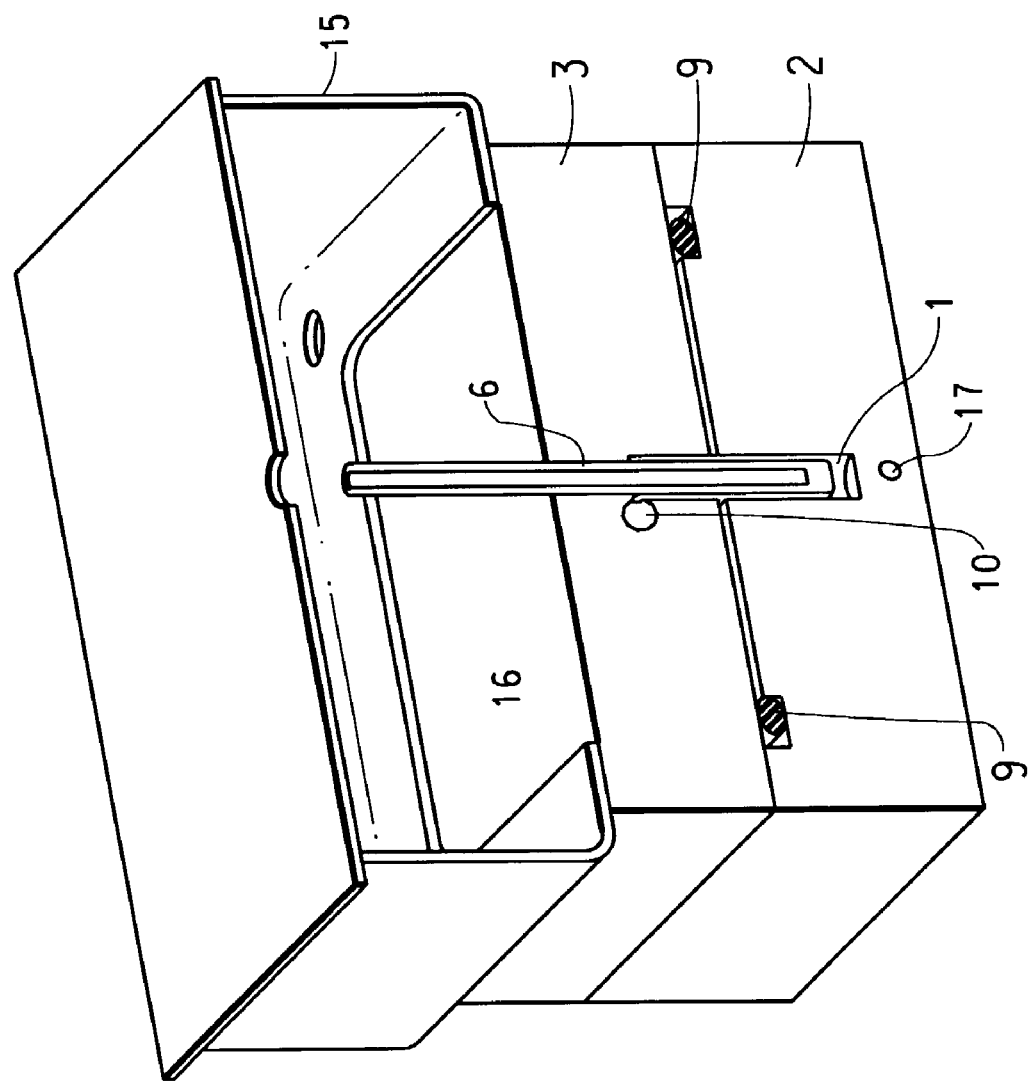
FIG. 5 is a cross-sectional view of the assembled apparatus as used in the Example.

The test sample (2.0 mg) was dissolved in dichloromethane and then transferred to the sublimation well. After evaporation of the solvent at room temperature, the sublimation apparatus was assembled, as shown in FIG. 5. The well plate 2 and finger plate 3 were 3.25 inches wide by 3.25 inches (82.5×82.5 mm) long. The well plate was 0.75 inches (19.1 mm) deep and the finger plate was 0.61 inches (15.5 mm) deep. The cylindrical well 1 was 0.5 inches (12.7 mm) deep and 0.25 inches (6.35 mm) in diameter. The cylindrical finger 6 was 0.188 inches (4.78 mm) in diameter, 2.49 inches (63.2 mm) long, and located 0.125 (3.18 mm) inches from the bottom of the well. A 2.36 inch (59.9 mm) long, 0.07 inch (1.78 mm) diameter hole 16 was drilled into the finger 6 to allow insertion of a thermocouple for monitoring the temperature of the finger. Another hole 17 was drilled in the well plate 2 under the well 1 to allow insertion of a thermocouple to monitor the temperature of the well. A Kalrez® perfluoroelastomer o-ring was used as the sealing means 9. A vacuum pump (not shown in drawing) was connected to the channel 10 (0.125 inches (3.18 mm) in diameter), and the apparatus was placed on top of a heating plate (VWR Brand Model 305 Hot Plate, not shown in drawing).

After assembly, the internal chamber was placed under positive nitrogen pressure. An ethylene glycol-water (1:1) mixture at −20° C. was circulated through the cooling bath using a Julabo FP88-MW recirculating chiller bath. Once the cold finger reached an equilibrium temperature of −4.5° C., the internal pressure was brought to $10 \times 10^{-3}$ torr. The initial temperature of the finger 6 was −4.5° C. and the initial temperature of the well plate 2 was 10.1° C. The temperatures were measured using digital thermometers inserted in holes 16 and 17. The temperature of the well plate was gradually raised for 45 minutes, until the temperature of the well plate was 232.4° C. and the temperature of the finger was 24.2° C. The heating plate was then turned off but the cooling solution continued to recirculate. After cooling 45 min., the cooling solution was drained, the apparatus was warmed to ambient temperatures, and channel 10 was slowly filled with nitrogen to achieve atmospheric pressure. The apparatus was disassembled and the luminescent sample was observed on the finger. No sample was detected in the well using either ambient light or UV.

What is claimed is:

1. An apparatus, comprising:
   a) a well-plate containing one well or a plurality of wells, each well having a bottom surface;
   b) a finger plate located above the well plate forming a plate free space, wherein the finger plate contains one or more recesses;
   c) one or more fingers located inside each recess, each finger having a bottom end having an end surface thereon, wherein each of the fingers extend downwards into one of the wells, forming a well space between each finger and the corresponding well and recess, wherein the well space and the plate free space together form a channel, the bottom end surface of each finger being positioned a predetermined distance from the bottom surface of the well;

d) a means for sealing the channel around the outside perimeter of the wells and fingers;

e) a means for heating the well plate; and f) means for cooling the fingers such that the fingers are at a lower temperature than the wells.

2. The apparatus of claim 1 wherein there is a plurality of wells.

3. The apparatus of claim 1 wherein the means for sealing the channel around the outside perimeter of the wells and fingers are selected from the group consisting of an o-ring and a gasket.

4. The apparatus of claim 3 wherein the sealing means is an o-ring comprised of perfluoroelastomer.

5. The apparatus of claim 3 further comprising one or more spacers between the finger plate and the well plate, thereby to define the predetermined distance between each finger bottom end surface and the bottom surface of the corresponding well.

6. An apparatus, comprising:

a) a well-plate containing one well or a plurality of wells;

b) a finger plate located above the well plate forming a plate free space, wherein the finger plate contains one or more recesses;

c) one or more fingers located inside each recess, each finger having a bottom end having an end surface thereon, wherein each of the fingers extend downwards into one of the wells, forming a well space between each finger and the corresponding well and recess, wherein the well space and the plate free space together form a channel, the bottom end surface of each finger being positioned a predetermined small distance from the bottom surface of the well;

d) a means for drawing a vacuum connected to the channel;

e) a means for sealing the channel around the outside perimeter of the wells and fingers such that the plate free space and continuous channel can maintain a vacuum;

f) a means for heating the well plate; and g) a means for cooling the fingers such that the fingers are at a lower temperature than the wells.

7. The apparatus of claim 6 wherein there is a plurality of wells.

8. The apparatus of claim 6 wherein the vacuum is at a pressure of at least $10^{-2}$ torr.

9. The apparatus of claim 6 wherein the means for sealing the channel around the outside perimeter of the wells and fingers is selected from the group consisting of an o-ring and a gasket.

10. The apparatus of claim 9 wherein the sealing means is an o-ring comprised of perfluoroelastomer.

11. The apparatus of claim 9 further comprising one or more spacers between the finger plate and the well plate, thereby to define the predetermined distance between each finger bottom end surface and the bottom surface of the corresponding well.

12. The apparatus of claim 6 further comprising a network of interconnected channels in the finger plate located between the recesses, with one or more openings from each recess to a channel.

13. A method for testing the sublimation potential of a compound, comprising:

I) placing one or more compounds in the bottom of one or more wells, wherein only one compound is placed in each well, and wherein said wells are located in an apparatus, comprising:

a) a well-plate containing one well or a plurality of wells, each well having a bottom surface;

b) a finger plate located above the well plate forming a plate free space, wherein the finger plate contains one or more recesses;

c) one or more fingers located inside each recess, each finger having a bottom end having an end surface thereon, wherein each of the fingers extend downwards into one of the wells, forming a well space between each finger and the corresponding well and recess; wherein the well space and the plate free space together form a channel, the bottom end surface of each finger being positioned a predetermined distance from the bottom surface of the well, the predetermined distance being:

1) sufficient that the bottom end surface of the finger does not contact the compound on the bottom surface of the well, and 2) less than a calculated mean free path $\lambda$ of the molecules of the compound;

d) a means for sealing the channel around the outside perimeter of the wells and fingers;

e) a means for heating the well plate; and f) a means for cooling the fingers such that the fingers are at a lower temperature than the wells;

II) cooling the fingers to a temperature of −20° C. to 100° C.

III) heating the wells to a temperature of 100° C. to 300° C.;

IV) removing the finger plate; and

V) detecting the presence of the each compound on the bottom end surface of each finger.

14. The method of claim 13 wherein there is a plurality of wells and a plurality of compounds.

15. The method of claim 13 wherein the means for sealing the channel around the outside perimeter of the wells and fingers is selected from the group consisting of an o-ring and a gasket.

16. The method of claim 15 wherein the sealing means is an o-ring comprised of perfluoroelastomer.

17. The method of claim 15 further comprising one or more spacers between the finger plate and the well plate, thereby to define the predetermined distance between each finger bottom end surface and the bottom surface of the corresponding well.

18. A method for testing the sublimation potential of a compound, comprising:

I) placing one or more compounds in the bottom of one or more wells, wherein only one compound is placed in each well, and wherein said wells are located in an apparatus, comprising:

a) a well-plate containing one well or a plurality of wells;

b) a finger plate located above the well plate forming a plate free space, wherein the finger plate contains one or more recesses;

c) one or more fingers located inside each recess, each finger having a bottom end having an end surface thereon, wherein each of the fingers extend downwards into one of the wells, forming a well space between each finger and the corresponding well and recess; wherein the well space and the plate free space together form a channel, the bottom end surface of each finger being positioned a predetermined distance from the bottom surface of the well, the predetermined distance being:
1) sufficient that the bottom end surface of the finger does not contact the compound on the bottom surface of the well, and
2) less than a calculated mean free path $\lambda$ of the molecules of the compound;
d) a means for drawing a vacuum connected to the channel;
e) a means for sealing the channel around the outside perimeter of the wells and fingers such that the plate free space and continuous channel can maintain a vacuum;
f) a means for heating the well plate; and
g) a means for cooling the fingers such that the fingers are at a lower temperature than the wells;
II) creating a vacuum within the channel;
III) cooling the fingers to a temperature of −20° C. to 100° C.;
IV) heating the wells to a temperature of 100° C. to 300° C.;
V) removing the finger plate; and
VI) detecting the presence of the each compound on the bottom end surface of each finger.

19. The method of claim 18 wherein there is a plurality of wells and a plurality of compounds.

20. The method of claim 18 wherein the vacuum is at a pressure of at least $10^{-2}$ torr.

21. The method of claim 18 wherein the means for sealing the channel around the outside perimeter of the wells and fingers is selected from the group consisting of an o-ring and a gasket.

22. The method of claim 21 wherein the sealing means is an o-ring comprised of perfluoroelastomer.

23. The method of claim 21 further comprising one or more spacers between the finger plate and the well plate.

24. The method of claim 18 further comprising a network of interconnected channels in the finger plate located between the recesses, with one or more openings from each recess to a channel, wherein the cross sectional area of the channels is greater than the adjacent cross sectional area of the plate free space.

25. The method of claim 13 wherein the calculated mean free path $\lambda$ of a molecule of the compound is defined by the equation $$\lambda = \frac{RT}{\sqrt{2}\,\pi d^2 N_a P}$$

where R is the gas constant, T is temperature, d is the diameter of the molecule, $N_a$ is Avogadro's number, and P is the pressure.

26. The method of claim 18 wherein the calculated mean free path $\lambda$ of a molecule of the compound is defined by the equation $$\lambda = \frac{RT}{\sqrt{2}\,\pi d^2 N_a P}$$

where R is the gas constant, T is temperature, d is the diameter of the molecule, $N_a$ is Avogadro's number, and P is the pressure.

* * * * *